United States Patent [19]

Tomiyama et al.

[11] Patent Number: 5,240,944
[45] Date of Patent: Aug. 31, 1993

[54] CYCLIC GUANIDINE DERIVATIVES, ANTI-ULCERATIVES AND METHOD OF MANUFACTURING THE SAME

[75] Inventors: Tsuyoshi Tomiyama; Akira Tomiyama; Tadashi Shirai, all of Sakaki; Shuuichi Wakabayashi, Koushoku; Tomoyuki Kawai, Nagano; Naoto Ueyama, Ueda; Motoharu Sonegawa, Nagano, all of Japan

[73] Assignee: Kotobuki Seiyaku Co. Ltd., Sakaki, Japan

[21] Appl. No.: 665,662

[22] Filed: Mar. 7, 1991

Related U.S. Application Data

[62] Division of Ser. No. 450,264, Dec. 13, 1989, Pat. No. 5,008,282.

[30] Foreign Application Priority Data

Dec. 28, 1988 [JP]  Japan ............................ 63-332550

[51] Int. Cl.$^5$ .................... C07C 235/30; A01N 43/40
[52] U.S. Cl. .................................. 514/322; 514/338; 514/393; 514/394; 546/199; 546/271; 548/302.1; 548/303.1
[58] Field of Search ............... 548/324; 546/190, 271; 514/393, 394, 322, 338, 339

[56] References Cited

U.S. PATENT DOCUMENTS 5,008,282  4/1991  Tomiyama et al. ................. 514/393

FOREIGN PATENT DOCUMENTS

| | | | |
|---|---|---|---|
| 1420951 | 4/1969 | Fed. Rep. of Germany ...... | 548/324 |
| 0138034 | 4/1985 | Fed. Rep. of Germany . | |
| 197708 | 8/1977 | U.S.S.R. ............................. | 514/394 |
| 753094 | 7/1981 | U.S.S.R. ............................. | 514/293 |

OTHER PUBLICATIONS

Biochemical and Biophysical Research Communications G. Racku, M. Bickel, H. W. Fehlhaber et al. pp. 477–484. Copyright 1985; vol. 128, No. 1. West Germany.

Primary Examiner—Alan L. Rotman
Assistant Examiner—Raymond Covington
Attorney, Agent, or Firm—Emmanuel J. Lobato; Robert E. Burns

[57] ABSTRACT

Derivatives of cyclic guanidine are disclosed, which are represented by the following formula:

A—S—R wherein A is

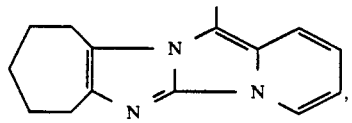

,

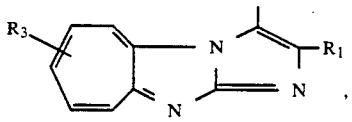

,

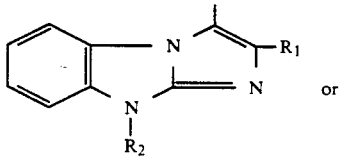 or

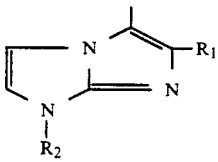

$R_1$ represent a lower alkyl or substituted phenyl or unsubstituted phenyl group; $R_2$ is a lower alkyl; $R_3$ is H or a lower alkyl; R is lower alkyl, alkenyl, alkynyl, alkanoyl, alkenoyl, dialkylaminoalkyl, cyanoalkyl, alkoxycarbonylalkyl, carboxylalkenyl, alkoxycarbonyl,
(Abstract continued on next page.)

alkoxyalkylcarbonyl, dialkylaminocarbonyl, dialkylaminothiocarbonyl, phenoxyalkylcarbonyl, piperidinoalkyl, pyridine carbonyl, substituted or unsubstituted benzoyl, or substituted or unsubstituted benzyl group.

The compounds of the present invention are useful as anti-ulcerative agents.

5 Claims, No Drawings

CYCLIC GUANIDINE DERIVATIVES, ANTI-ULCERATIVES AND METHOD OF MANUFACTURING THE SAME

This is a divisional of application Ser. No. 07/450,264, filed Dec. 13, 1989, now U.S. Pat. No. 5,008,282.

BACKGROUND OF THE INVENTION

This invention relates to new cyclic guanidine derivatives and their acid addition salts, a method of their synthesis and their use as potent anti-ulceratives.

There have heretofore been used conventional anti-gastric ulcerative materials which may inhibit the secretion of gastric juice principally by their anti-cholinergic or anti-histaminic activities. Under the present circumstances, it is desirable to have material which are effective to inhibit the secretion of gastric juice by preventing (H+, K+) ATPase in the process of formation of HCl, where Cl− acts on H+ secreted by acid (H+, K+) ATPase in the gastric membrane.

SUMMARY OF THE INVENTION

The principal object of the present invention is the provision of compounds having (H+, K+) ATPase inhibitory activities.

Another object of the present invention is the provision of pharmaceutical compositions useful as anti-peptic ulcerative agents.

Still other objects of the present invention are the provision of cyclic guanidine derivatives and a method for the manufacture thereof.

These and other objects of the invention will become apparent from the following description.

DETAILED DESCRIPTION OF THE INVENTION

This invention relates to new cyclic guanidine derivatives and their acid-addition salts, and a method of their synthesis and use as potent anti-ulcerative agents.

The compounds of this invention are represented by the general formula (I):

$$A-S-R \quad (I)$$

wherein A is pyrido [1′, 2′:3,4]imidazo[1,2a]-7,8,9,10,11-pentahydrocycloheptimidazole-13-yl (formula Ia);

(Ia)

2-Substituted-cyclohept[d]imidazo[1,2-a]imidazole-3-yl (general formula Ib);

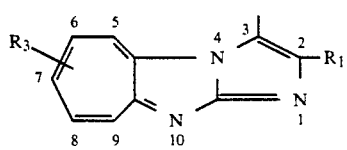

(Ib)

($R_1$ represents a lower alkyl or substituted phenyl or unsubstituted phenyl group and $R_3$ is H or a lower alkyl group.) 2-Substituted-9-alkyl-9H-imidazo[1,2-a]benzimidazole-3-yl (general formula Ic);

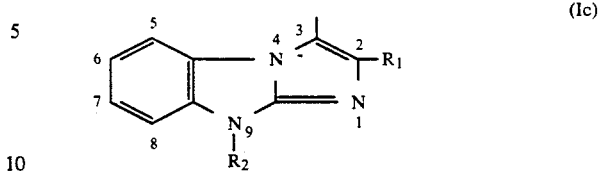

(Ic)

($R_1$ is same as mentioned above. $R_2$ is a lower alkyl group.) Or 6-Substituted-1-alkyl-1H-imidazo[1,2-a]imidazole-5-yl (general formula Id);

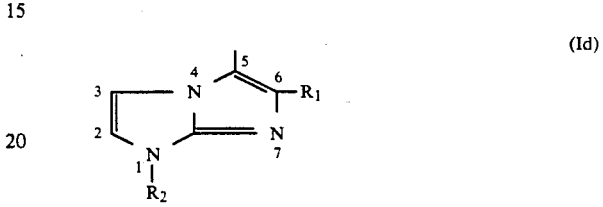

(Id)

($R_1$ and $R_2$ are same as mentioned above.); R is a lower alkyl, alkenyl, alkynyl, alkanoyl, alkenoyl, dialkylaminoalkyl, cyanoalkyl, alkoxycarbonylalkyl, carboxyalkenyl, alkoxycarbonyl, alkoxyalkylcarbonyl, dialkylaminocarbonyl, dialkylaminothiocarbonyl, phenoxyalkylcarbonyl, piperidinoalkyl, pyridine carbonyl, substituted or unsubstituted benzoyl or substituted or unsubstituted benzyl group.

In this invention, alkyl, alkenyl, alkynyl, alkanoyl, alkenoyl and alkoxy means corresponding group of $C_1 \sim C_5$, respectively. For example, lower alkyl is mentioned such as methyl, ethyl, propyl, isopropyl, butyl, isobutyl, pentyl, isopentyl etc. And other groups are same as defined in lower alkyl groups.

Consequently, dialkylaminoalkyl group means dimethylaminoethyl, diethylamioethyl etc. and a substituted phenyl group, for example, means lower-alkylphenyl, alkoxyphenyl or halogenophenyl group.

The compound of general formula (I) can be obtained by reaction of the compound shown by the general formula (II) with a compound of the general formula (III).

$$[A-S-]_2 \quad (II)$$

wherein A is the same as mentioned above.

$$X-R \quad (III)$$

wherein X is a halogen atom and R is the same as mentioned above.

The compounds shown by the general formula (II) are new compounds and can be prepared by reaction of the compounds of general formula (IV) with sulfur monohalide of general formula (V) according to the method of disulfide compound preparation [R. J. Laufer, U.S. Pat. No. 3,479,407 (Chem. Abst. 72, 31445 g)]

$$A-H \quad (IV)$$

wherein A is same as mentioned above.

$$X-S-S-X \quad (V)$$

wherein X is halogen atom.

Among the compounds shown in general formula (IV), in case A is shown in formula (Ia), the compound of the general formula (IV) is corresponding to pyrido[1', 2':3,4]imidazo[1,2-a]-7,8,9,10,11-pentahydrocycloheptimidazole (IVa), which is a new compound and obtained as follows.

2-hydroxy cycloheptimidazole (VI) was hydrogenated to a compound (VII) and a compound (VII) was chlorinated to a compound (VIII). By reacting the compound (VIII) with 2-picolyl chloride hydrochlolide, a compound (IX) was obtained. The compound (IX) was cyclized in ethanol-HCl, and obtained was the objective compound (IVa).

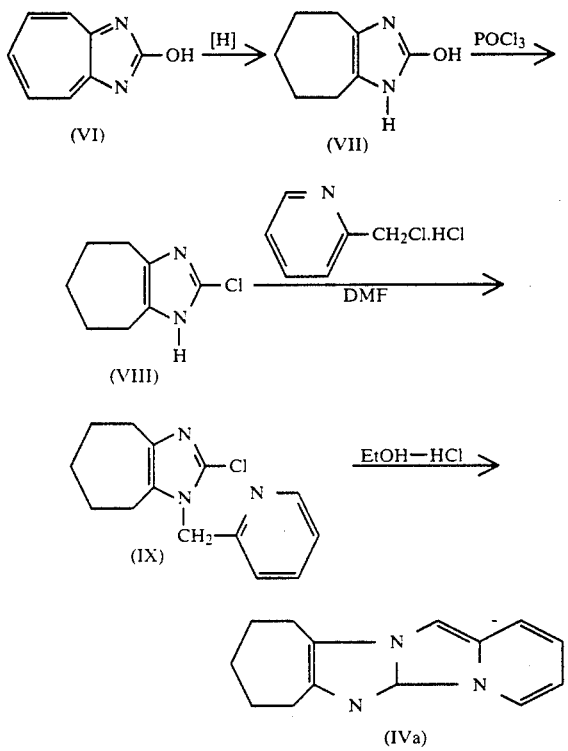

The compounds shown by the formula (IVa) and the general formula (II) for starting material are new compounds and some of them are exemplified as follows.
(1) Pyrido[1',2':3,4]imidazo[1,2-a]-7,8,9,10,11-pentahydrocycloheptimidazole.
(2) Bis 13,13'-pyrido[1',2':3,4]imidazo[1,2-a]-7,8,9,10,11-pentahydrocycloheptimidazole disulfide.
(3) Bis 3,3'-2-phenyl-cyclohept[d]imidazo[1,2-a]imidazole disulfide.
(4) Bis 3,3'-2-(4-methoxyphenyl)-cyclohept[-d]imidazo[1,2-a]imidazol disulfide.
(5) Bis 3,3'-2-(4-fluorophenyl)-cyclohept[d]imidazo[1,2-a]imidazol disulfide.
(6) Bis 3,3'-2-(4-chlorophenyl)-cyclohept[-d]imidazo[1,2-a]imidazol disulfide.
(7) Bis 3,3'-2-phenyl-7-isopropyl-cyclohept[-d]imidazo[1,2-a]imidazol disulfide
(8) Bis 3,3'-2-(4-fluorophenyl)-7-isopropyl-cyclohept[-d]imidazo[1,2-a]imidazol disulfide.
(9) Bis 3,3'-2-methyl-cyclohept[d]imidazo[1,2-a]imidazole disulfide.
(10) Bis 3,3'-2-methyl-7-isopropyl-cyclohept[-d]imidazo[1,2-a]imidazol disulfide.
(11) Bis 3,3'-2,9-dimethyl-9H-imidazo[1,2-a]benzimidazole disulfide.
(12) Bis 3,3'-2-phenyl-9-methyl-9H-imidazo[1,2-a]benzimidazole disulfide.
(13) Bis 5,5'-1,6-dimethyl-1H-imidazo[1,2-a]imidazole disulfide.
(14) Bis 5,5'-1-methyl-6-phenyl-1H-imidazo[1,2-a]imidazole disulfide.

The above-mentioned compounds numbered from (1), (2), to (14) will be refered to hereinafter, as compound (1), compound (2), compound (14) respectively.

In the general formula (IV), in case A is shown in the formula (Ib) as 2-substituted-cyclohept[d]imidazo[1,2-a]imidazole, this compound can be obtained according to the method of N. Abe et al. [Bull. Chem. Soc. Japan, 56, 3703–14, (1983)].

In this method, a compound which has a substituted phenyl group as $R_1$ in the general formula (IV), from which compound (4), (5) or (6) is derived, is obtained by using a α-bromoacetophenone derivative having said substituted phenyl group.

A 2-methyl substituted compound of the general formula (IV)—a starting material for compound (9)—is prepared by using a chloroacetone instead of said α-bromoacetophenone.

A starting material for compound (7), (8) or (10) is obtained by using a substituted 2-amino-cycloheptimidazol.

In the general formula (VI): A-H, in case A is shown in the formula (Ic) as 2-substituted-9-alkyl-9H-imidazo[1,2-a]benzimidazole, this compound can be prepared according to the procedure of A. M. Simonov et al. [Khim. Geterotsikl. Soedin. 1970, 838–41 (Chem. Abst. 73, 109739f)]

Furthermore in general formula (IV), in case A is shown in formula (Ia) as 6-substituted-1-alkyl-1H-imidazo[1,2-a]imidazole, this compound is obtained by the method of L. F. Miller et al. [J. Med. Chem. 15, 415, (1972)].

The reaction of compounds of general formula (II) with the compound of general formula (III) can be carried out in the presence of hydrogenating agents. As the hydrogenating agents used in this reactions, NaBH is preferable but other hydride compounds can be applied. As the solvent used in this reactions, alcohols and tetrahydrofuran are mentioned. Furthermore inert solvents in this reaction can be available. The reaction proceeds at ambient or elevated temperature.

The reaction products are refined in the usual manner such as recrystallization or column chromatography.

The compounds related to the general formula (I) are exemplified as follows.
(15) 13-Cyanomethylthio-pyrido[1',2':3,4]imidazo[1,2-a]-7,8,9,10,11-pentahydro-cycloheptimidazole.
(16) 13-(2-Propenyl)thio-pyrido[1',2':3,4]imidazo[1,2-a]-7,8,9,10,11-pentahydro-cycloheptimidazole.
(17) 13-((E,Z)-2-Butenyl)thio-pyrido[1',2':3,4 ]imidazo[1,2-a]-7,8,9,10,11-pentahydro-cycloheptimidazole.
(18) 13-(2-Propynyl)thio-pyrido[1',2':3,4]imidazo[1,2-a]-7,8,9,10,11-pentahydro-cycloheptimidazole.
(19) 13-(2-Butynyl)thio-pyrido[1',2':3,4]imidazo[1,2-a]-7,8,9,10,11-pentahydro-cycloheptimidazole.
(20) 13-(Acetyl)thio-pyrido[1',2':3,4]imidazo[1,2-a]-7,8,9,10,11-pentahydro-cycloheptimidazole fumarate.
(21) 13-(Propionyl)thio-pyrido[1',2':3,4]imidazo[1,2-a]-7,8,9,10,11-pentahydro-cycloheptimidazole fumarate.

(22) 13-(2-Dimetylaminoethyl)thio-pyrido[1',2':3,4]imidazo[1,2-a]-7,8,9,10,11-pentahydro-cycloheptimidazole.
(23) 13-[2-(1-Piperidino)ethyl]thio-pyrido[1',2':3,4]imidazo[1,2-a]-7,8,9,10,11-pentahydro-cycloheptimidazole.
(24) 13-(Methoxycarbonylmethyl)thio-pyrido[1',2':3,4]imidazo[1,2-a]-7,8,9,10,11-pentahydro-cycloheptimidazole.
(25) 13-(Dimethylaminocarbonyl)thio-pyrido[1',2':3,4]imidazo[1,2-a]-7,8,9,10,11-pentahydro-cycloheptimidazole.
(26) 13-(Dimethylaminothiocarbonyl)thio-pyrido[1',2':3,4]imidazo[1,2-a]-7,8,9,10,11-pentahydro-cycloheptimidazole.
(27) 13-(2-(N-Propionylamino)benzyl)thio-pyrido[1',2':3,4]imidazo[1,2-a]-7,8,9,10,11-pentahydro-cycloheptimidazole.
(28) 3-(Methyl)thio-2-phenyl-cyclohept[d]imidazo[1,2-a]imidazole.
(29) 3-(Propyl)thio-2-phenyl-cyclohept[d]imidazo[1,2-a]imidazole.
(30) 3-(2-Propenyl)thio-2-phenyl-cyclohept[d]imidazo[1,2-a]imidazole.
(31) 3-((E,Z)-2-Butenyl)thio-2-phenyl-cyclohept[d]imidazo[1,2-a]imidazole.
(32) 3-(2-Propynyl)thio-2-phenyl-cyclohept[d]imidazo[1,2-a]imidazole.
(33) 3-(2-Butynyl)thio-2-phenyl-cyclohept[d]imidazo[1,2-a]imidazole.
(34) 3-(Acetyl)thio-2-phenyl-cyclohept[d]imidazo[1,2-a]imidazole.
(35) 3-(Propionyl)thio-2-phenyl-cyclohept[d]imidazo[1,2-a]imidazole.
(36) 3-(Pivaloyl)thio-2-phenyl-cyclohept[d]imidazo[1,2-a]imidazole.
(37) 3-(Acryloyl)thio-2-phenyl-cyclohept[d]imidazo[1,2-a]imidazole.
(38) 3-(Crotonoyl)thio-2-phenyl-cyclohept[d]imidazo[1,2-a]imidazole.
(39) 3-(2-Dimethylaminoethyl)thio-2-phenyl-cyclohept[d]imidazo[1,2-a]imidazole.
(40) 3-(2-(1-Piperidino)ethyl)thio-2-phenyl-cyclohept[d]imidazo[1,2-a]imidazole.
(41) 3-(Cyanomethyl)thio-2-phenyl-cyclohept[d]imidazo[1,2-a]imidazole.
(42) 3-(Methoxycarbonylmethyl)thio-2-phenyl-cyclohept[d]imidazo[1,2-a]imidazole.
(43) 3-(Methoxyacetyl)thio-2-phenyl-cyclohept[d]imidazo[1,2-a]imidazole.
(44) 3-(3-Methoxypropionyl)thio-2-phenyl-cyclohept[d]imidazo[1,2-a]imidazole.
(45) 3-(Dimethylaminocarbonyl)thio-2-phenyl-cyclohept[d]imidazo[1,2-a]imidazole.
(46) 3-(Dimethylaminothiocarbonyl)thio-2-phenyl-cyclohept[d]imidazo[1,2-a]imidazole.
(47) 3-(Ethoxycarbonyl)thio-2-phenyl-cyclohept[d]imidazo[1,2-a]imidazole.
(48) 3-(Picolinoyl)thio-2-phenyl-cyclohept[d]imidazo[1,2-a]imidazole.
(49) 3-(Benzoyl)thio-2-phenyl-cyclohept[d]imidazo[1,2-a]imidazole.
(50) 3-(2-(N-Propionylamino)benzyl)thio-2-phenyl-cyclohept[d]imidazo[1,2-a]imidazole.
(51) 3-(butyryl)thio-2-phenyl-cyclohept[d]imidazo[1,2-a]imidazole
(52) 3-(propionyl)thio-2-phenyl-7-isopropyl-cyclohept[d]imidazo[1,2-a]imidazole.
(53) 3-(valeryl)thio-2-phenyl-7-isopropyl-cyclohept[d]imidazo[1,2-a]imidazole.
(54) 3-(propionyl)thio-2-(4-methoxyphenyl)-cyclohept[d]imidazo[1,2-a]imidazole.
(55) 3-(acetyl)thio-(4-fluorophenyl)-cyclohept[d]imidazo[1,2-a]imidazole.
(56) 3-(propionyl)thio-2-(4-fluorophenyl)-cyclohept[d]imidazo[1,2-a]imidazole.
(57) 3-(acetyl)thio-2-(4-chlorophenyl)-cyclohept[d]imidazo[1,2-a]imidazole.
(58) 3-(propionyl)thio-2-(4-chlorophenyl)-cyclohept[d]imidazo[1,2-a]imidazole.
(59) 3-(propionyl)thio-2-(4-fluorophenyl)-7-isopropyl-cyclohept[d]imidazo[1,2-a]imidazole.
(60) 3-((E)-2-Carboxy-2-ethenyl)thio-2-methyl-cyclohept[d]imidazo[1,2-a]imidazole.
(61) 3-(2-Propenyl)thio-2-methyl-cyclohept[d]imidazo[1,2-a]imidazole.
(62) 3-((E,Z)-2-Butenyl)thio-2-methyl-cyclohept[d]imidazo[1,2-a]imidazole.
(63) 3-(Propinyl)thio-2-methyl-cyclohept[d]imidazo[1,2-a]imidazole.
(64) 3-(Butynyl)thio-2-methyl-cyclohept[d]imidazo[1,2-a]imidazole.
(65) 3-(Acetyl)thio-2-methyl-cyclohept[d]imidazo[1,2-a]imidazole.
(66) 3-(Propionyl)thio-2-methyl-cyclohept[d]imidazo[1,2-a]imidazole.
(67) 3-(Butyryl)thio-2-methyl-cyclohept[d]imidazo[1,2-a]imidazole.
(68) 3-(Pivaloyl)thio-2-methyl-cyclohept[d]imidazo[1,2-a]imidazole.
(69) 3-(Crotonoyl)thio-2-methyl-cyclohept[d]imidazo[1,2-a]imidazole.
(70) 3-(Dimethylaminoethyl)thio-2-methyl-cyclohept[d]imidazo[1,2-a]imidazole.
(71) 3-(2-(1-Piperidino)ethyl)thio-2-methyl-cyclohept[d]imidazo[1,2-a]imidazole.
(72) 3-(Methoxyacetyl)thio-2-methyl-cyclohept[d]imidazo[1,2-a]imidazole.
(73) 3-(Dimethylaminocarbonyl)thio-2-methyl-cyclohept[d]imidazo[1,2-a]imidazole.
(74) 3-(Dimethylaminothiocarbonyl)thio-2-methyl-cyclohept[d]imidazo[1,2-a]imidazole.
(75) 3-(3-MethoxyPropionyl)thio-2-methyl-cyclohept[d]imidazo[1,2-a]imidazole.
(76) 3-(Picolinoyl)thio-2-methyl-cyclohept[d]imidazo[1,2-a]imidazole.
(77) 3-(Benzoyl)thio-2-methyl-cyclohept[d]imidazo[1,2-a]imidazole.
(78) 3-(2-(N-Propionylamino)benzyl)thio-2-methyl-cyclohept[d]imidazo[1,2-a]imidazole.
(79) 3-(Cyanomethyl)thio-2-methyl-cyclohept[d]imidazo[1,2-a]imidazole.
(80) 3-(Methoxycarbonylmethyl)thio-2-methyl-cyclohept[d]imidazo[1,2-a]imidazole.
(81) 3-(isobutyryl)thio-2-methyl-cyclohept[d]imidazo[1,2-a]imidazole.
(82) 3-(valeryl)thio-2-methyl-cyclohept[d]imidazo[1,2-a]imidazole.
(83) 3-(4-methoxybenzoyl)thio-2-methyl-cyclohept[d]imidazo[1,2-a]imidazole.
(84) 3-(4-fluorobenzoyl)thio-2-methyl-cyclohept[d]imidazo[1,2-a]imidazole.
(85) 3-(4-chlorobenzoyl)thio-2-methyl-7-isopropyl-cyclohept[d]imidazo[1,2-a]imidazole.
(86) 3-(benzoyl)thio-2-methyl-7-isopropyl-cyclohept[d]imidazo[1,2-a]imidazole.

(87) 3-(Propionyl)thio-2-phenyl-9-methyl-9H-imidazo[1,2-a]benzimidazole.
(88) 3-(Propionyl)thio-2,9-dimethyl-9H-imidazo[1,2-a]benzimidazole.
(89) 3-(Methoxyacetyl)thio-2-phenyl-9-methyl-9H-imidazo[1,2-a]benzimidazole.
(90) 5-(Propionyl)thio-6-phenyl-1-methyl-1H-imidazo[1,2-a]imidazole.
(91) 5-(Propionyl)thio-1,6-dimethyl-1H-imidazo[1,2-a]imidazole.
(92) 5-(Phenoxyacetyl)thio-6-phenyl-1-methyl-1H-imidazo[1,2-a]imidazole.

The above-mentioned compounds numbered from 15 to 92 will be referred to hereinafter, as compound 92 respectively.

The compounds of general formula (I) of this invention have excellent $(H^+, K^+)$ATPase inhibition effects as shown later and the compounds of general formula (I) can be applied as anti-ulceratives in the form of their free bases or their pharmaceutically acceptable acid-addition salts, for instance, mineral acids such as hydrochloric acid, sulfuric acid or organic acid such as succinic acids or fumaric acid.

Concerning dosage forms, the compounds of the present invention can be administered perorally or parenterally. Doses to be administered to particular patients are various, depending on the patient's condition, patient's response or age. Usually dosage of the compound is from 10 mg to 500 mg for an adult a day.

The following examples illustrate a few antiulcerative dosage unit compositions comprising the compound of the present invention.

| (Dosage example 1) Granules | |
|---|---|
| Compound 18 | 50 mg |
| Lactose | 40 mg |
| Cornstarch | 57 mg |
| Methyl cellulose | 3 mg |
| Total | 150 mg |

The mixture of these compositions is granulated in a conventional manner.

| (Dosage example 2) Tablet | |
|---|---|
| Compound 48 | 30 mg |
| Lactose | 30 mg |
| Cornstarch | 45 mg |
| Magnesium stearate | 2 mg |
| Total | 110 mg |

The mixture of these compositions is compressed into 110 mg tablet in a conventional manner.

The following examples show pharmacological activity of the compounds of this invention and their preparation.

Pharmacological data 1

Inhibitory activities of gastric-acid secretion in the acute fistula rat.

Determination of gastric-acid secretion is performed by the method of Y. Goto et al. (Expenentia 32, 946, (1976)). Male Wistar rats are anesthetized with urethane (1.2 g/kg, i.p.) 2 hours after the oral administration of compounds. A dual polyethylene cannula is introduced into the gastric lumen after ligation of the pylorus and the esophagus. The stomach is rinsed with 5 ml of saline through the gastric cannula at 15 min interval. The acid output during 15 minutes period is titrated with 0.01N NaOH. Histamine.2HCl (10 mg/kg, s.c.) is administered as a secretory agent 4 hours after the administration of compounds.

The inhibitory percent of compounds on histamine-stimulated acid secretion is calculated and the results are shown in table I.

TABLE 1

| Compd. NO. | Dose(mg/Kg) | Total acid inhibition |
|---|---|---|
| 21 | 50 | 64.9 |
| 34 | 50 | 76.6 |
| 35 | 50 | 54.0 |
| 37 | 50 | 51.5 |
| 38 | 50 | 63.4 |
| 43 | 50 | 53.8 |
| 44 | 50 | 80.7 |
| 53 | 50 | 73.7 |
| 65 | 50 | 68.8 |
| 66 | 50 | 63.7 |
| 68 | 50 | 73.9 |
| 69 | 50 | 83.5 |
| 76 | 50 | 83.7 |
| 77 | 50 | 82.5 |
| 81 | 50 | 79.8 |
| 82 | 50 | 81.2 |
| 87 | 50 | 53.8 |
| 92 | 50 | 65.6 |

Pharmacological data 2

Inhibition of $(H^+,K^+)$ATPase activities. Inhibition of $(H^+,K^+)$ATPase activities is determined by the method of F. Fellenius et al., [Nature 290, 159–61, (1981)]. $(H^+,K^+)$ATPase is prepared from the pig gastric mucosa and the test compound is incubated with 2 mM of ATPase, 40 mM of tris-buffer (pH 7.4), 2 mM of $MgCl_2$ and 10 mM of KCl at 37° C. Inorganic phosphate occurring by stimulation of ATPase is determined. The results are shown in table 2.

TABLE 2

| Compd. No. | $(H^+, K^+)$ ATPase $IC_{50}$ ($\mu$) |
|---|---|
| 16 | 16.5 |
| 18 | 3.06 |
| 19 | 47.3 |
| 21 | 18.1 |
| 23 | 91.3 |
| 34 | 2.47 |
| 35 | 10.5 |
| 37 | 2.20 |
| 38 | 13.3 |
| 43 | 2.23 |
| 44 | 8.75 |
| 48 | 2.72 |
| 53 | 1.95 |
| 55 | 1.40 |
| 57 | 0.79 |
| 66 | 17.5 |
| 69 | 22.7 |
| 72 | 5.9 |
| 75 | 55.1 |
| 81 | 2.79 |
| 87 | 25.8 |
| 92 | 16.0 |

$IC_{50}$:Concentration of 50% inhibition

EXAMPLE 1

Pyrido[1',2':3,4]imidazo[1,2-a]-7,8,9,10,11-pentahydrocyclohept imidazole (Compd. 1)

(1) 1,4,5,6,7,8-hexahydro-2-hydroxy-cycloheptimidazole

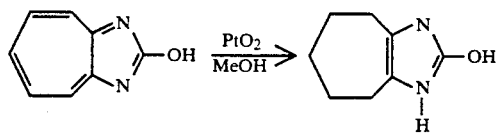

A solution of 2-Hydroxy-cycloheptimidazole (16.0 g) in methanol was stirred vigorously with platinum oxide (0.2 g) in the hydrogen stream. An off-white suspended solution obtained after 16 hrs, was refluxed and filtered. The insoluble material was extracted again with hot methanol (200 ml) and filtered. The combined filtrate was concentrated in reduced pressure. Obtained yellow powder was washed with ethanol (50 ml) and filtered. 14.6 g of the desired compound was obtained. m.p. 272° C./dec.

(2) 2-Chloro-1,4,5,6,7,8-hexahydro-cycloheptimidazole

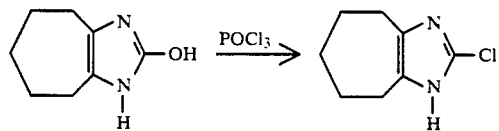

The compound (3.8 g) obtained from above mentioned procedure (1), was reacted with phosphorus oxychloride (49.7 g) and dimethylaniline (4.03 g) at 80° C. overnight. The reacted solution was concentrated by reduced pressure and the residue was poured on the ice water. After neutralized with NaHCO$_3$, the solution was extracted with chloroform. The solvent was evaporated, then the residue was purified with silica gel chromatography [eluent; AcOEt (ethyl acetate)] 1.15 g of the desired compound was obtained as white needle. m.p. 214.0°-215.3° C.

(3) 1-Picolyl-2-chloro-4,5,6,7,8-pentahydro-cycloheptimidazole

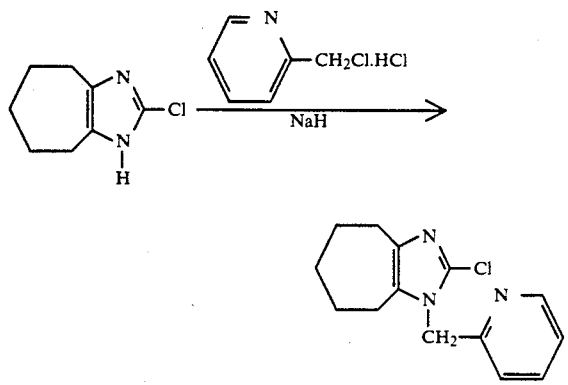

The compound (3.5 g) obtained from above mentioned procedure (2), was dissolved in DMF (30 ml), NaH (55%, 2.5 g) was added to this solution and stirred for 10 min. at room temperature. 2-Picolylchloride hydrochloride (3.4 g) was added to the above solution and reacted for 1.5 hrs at room temperature. The reaction mixture was poured onto the saturated NaCl solution (150 ml) and extracted with AcOEt (200 ml). After it was washed with water, dried (Na$_2$SO$_4$) and concentrated under reduced pressure. The residue was purified with silica gel chromatography [eluent; AcOEt:Hexane(1:1)] and 4.7 g of colorless oil was obtained.

M.S. (m/e): 261(M+), 226(B.P.), 208, 169, 143, 118, 93, 78, 65, 51. IR(cm$^{-1}$): 2914, 2842, 1590, 1467, 1434, 1395, 1347, 750, 681.

(4) Pyrido[1',2':3,4]imidazo[1,2-a]-7,8,9,10,11-pentahydrocycloheptimidazole

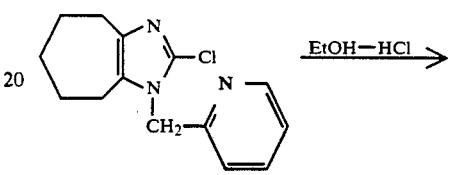

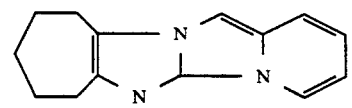

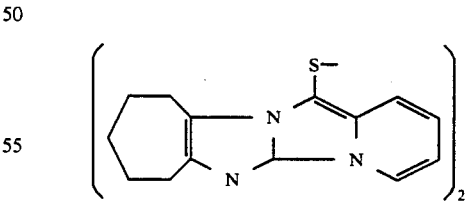

A mixture of the compound (8.6 g) obtained from above mentioned procedure (3) and a solution of 12% HCl-EtOH (60 ml) in sealed tube was reacted for 0.5 hr at room temperature then 17 hrs. at 80° C. After cooling, the reaction mixture was concentrated at reduced pressure. water (100 ml) was added to the residue and made alkaline with Na$_2$CO$_3$, then extracted with ether (200 ml). After removed the solvent, it was purified with silica gel chromatography (eluent; AcOEt). 6.7 g of the desired compound (greenish yellow powder) was obtained. m.p. 113.5°-114.5° C.

M.S. (m/e): 225(M+, B.P.), 196, 171, 132, 105, 91, 78, 65. IR(KBr, cm$^{-1}$): 3094, 2904, 2836, 1629, 1596, 1443, 1314, 726.

EXAMPLE 2

Bis 13,13'-pyrido[1',2':3,4]imidazo[1,2-a]-7,8,9,10,11-pentahydrocycloheptimidazole disulfide (Compd. 2)

Sulfur monochloride (0.077 g) was dropwise added to the dissolved compd. 1 (0.32 g) in THF (20 ml) under water cooling. Then, the mixture was stirred for 2 hrs. at room temperature and allowed to stand overnight. The obtained pricipitates were purified with silica gel column chromatography by eluted CHCl$_3$: MeOH (20:1). 0.268 g of the desired compound was obtained (74%). m.p. 174°-176° C./dec.

M.S. (m/e): 256(M+/2), 223, 122(B.P.), 105, 91, 78. IR(cm$^{-1}$): 2914, 1575, 1212, 750, 666.

The following compounds were obtained as same manner as Example 2.

EXAMPLE 3

Bis 3,3'-2-phenyl-cyclohept[d]imidazo[1,2-a]imidazole disulfide

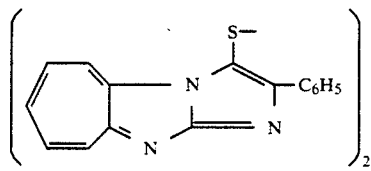

(Compd. 3)

m.p. 250° C.

EXAMPLE 4

Bis 3,3'-2-(4-methoxyphenyl)-cyclohept[d]imidazo[1,2-a]imidazole disulfide

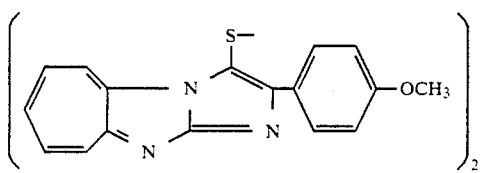

(Compd. 4)

m.p. 222-224° C.

EXAMPLE 5

Bis 3,3'-2-(4-fluorophenyl)-cyclohept[d]imidazo[1,2-a]imidazole disulfide

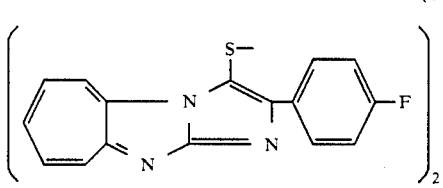

(Compd. 5)

m.p. above 280° C.

EXAMPLE 6

Bis 3,3'-2-(4-chlorophenyl)-cyclohept[d]imidazo[1,2-a]imidazole disulfide

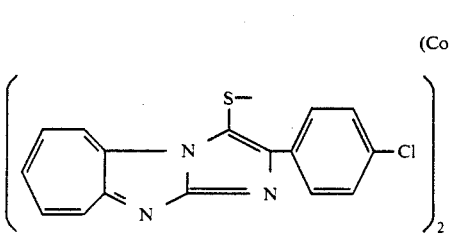

(Compd. 6)

m.p. above 280° C.

EXAMPLE 7

Bis 3,3'-2-phenyl-7-isopropyl-cyclohept[d]imidazo[1,2-a]imidazole disulfide

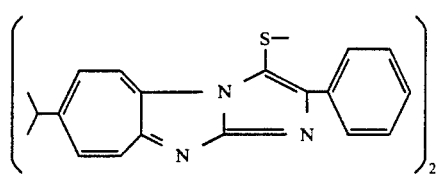

(Compd. 7)

m.p. 198-199° C.

EXAMPLE 8

Bis 3,3'-2-(4-fluorophenyl)-7-isopropyl-cyclohept[d]imidazo[1,2-a]imidazole disulfide

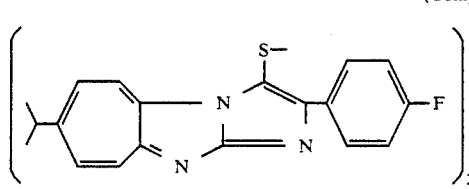

(Compd. 8)

m.p. 122-124° C.

EXAMPLE 9

Bis 3,3'-2-methyl-cyclohept[d]imidazo[1,2-a]imidazole disulfide

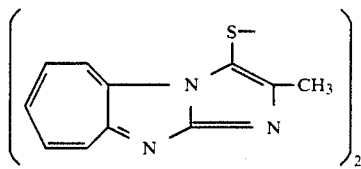

(Compound. 9)

m.p. 213° C. dec.

EXAMPLE 10

Bis 3,3'-2-methyl-7-isopropyl-cyclohept[d]imidazo[1,2-a]imidazole disulfide

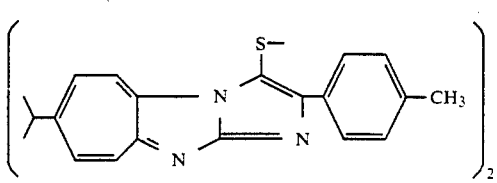

(Compd. 10)

m.p. 183° C. (decomp.)

EXAMPLE 11

Bis 3,3'-2,9-dimethyl-9H-imidazo[1,2-a]benzimidazole disulfide (Compound. 11)

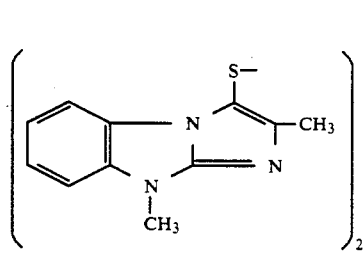

m.p. 181–183° C.

EXAMPLE 12

Bis 3,3'-2-phenyl-9-methyl-9H-imidazo[1,2-a]benzimidazole disulfide (Compound. 12)

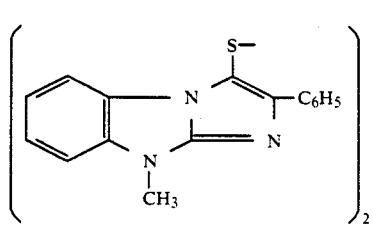

m.p. 208–210° C.

EXAMPLE 13

Bis 5,5'-1,6-dimethyl-1H-imidazo[1,2-a]imidazole disulfide (Compound. 13)

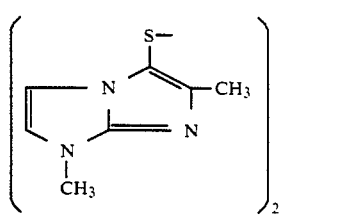

m.p. 146–148° C.

EXAMPLE 14

Bis 5,5'-1-methyl-6-phenyl-1H-imidazo[1,2-a]imidazole disulfide (Compound. 14)

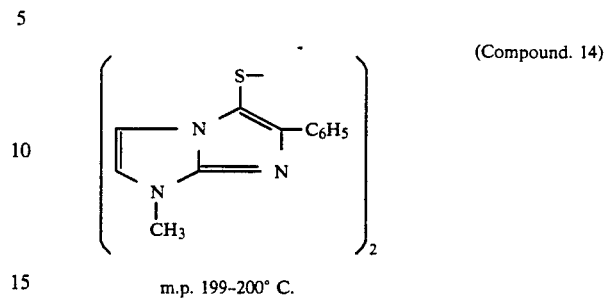

m.p. 199–200° C.

EXAMPLE 15

13-Cyanomethylthio-pyrido[1',2':3,4]imidazo[1,2-a]-7,8,9,10,11-pentahydro-cycloheptimidazole (Compound. 15)

NaBH$_4$ was added at room temperature to the dissolved compd. 2 (0.512 g) in THF (9 ml) and MeOH (0.05 ml). After the mixture was stirred for 5 minutes, bromoacetonitrile (0.14 ml) was added and reacted for 30 minutes. To the resultant solution, saturated ammonium chloride solution was added and stirred for 1 hr, then extracted with AcOEt. The AcOEt solution was washed with satd. NaCl, dried (Na$_2$SO$_4$) and evaporated the solvent. The residue was purified with silica gel chromatography [eluent; AcOEt:hexane (5:2)] 0.33 g (y 55.7%) of the desired compound was obtained as yellow crystalline. m.p. 145°–147° C.

M.S. (m/e): 296(M$^+$), 256(B.P.), 223, 196, 122, 78, 51.
IR(KBr, cm$^{-1}$): 3256, 2914, 2842, 1590, 1515, 1311, 741.
N.M.R. (): 1.6–2.1(6H,m,CH$_2$×3), 2.7–3.1(2H,m,CH$_2$), 3.1–3.4(2H,m,CH$_2$), 3.351(2H,s,SCH$_2$), 6.3–6.6(1H,t-like), 6.8–7.1(1H,m), 7.4–7.6(1H,d), 7.9–8.2(1H,d-like).

The following compounds in table 3 were obtained as the same manner as Example 15.

TABLE 3

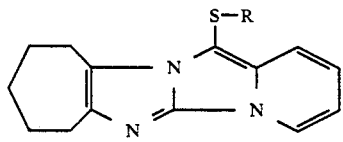

| Compds. No. | R | m.p. (°C.) | M.S. (m/e) |
|---|---|---|---|
| 16 | —CH$_2$—CH=CH$_2$ | 59–60 | 297 (M$^+$) |
| 17 | —CH$_2$—CH=CH—CH$_3$ | 107.5–109 | 311 (M$^+$) |
| 18 | —CH$_2$—C≡CH | 85–86.5 | 295 (M$^+$) |
| 19 | —CH$_2$—C≡C—CH$_3$ | 79–79.5 | 309 (M$^+$) |
| 20 | —COCH$_3$.fumarate | 163 (dec.) | 299 (M$^+$-fumaric |

TABLE 3-continued

| Compds. No. | | | | m.p. (°C.) | M.S. (m/e) |
|---|---|---|---|---|---|
| | | | | | acid) |
| 21 | —COC$_2$H$_5$.fumarate | | | 164 (dec.) | 313 (M$^+$-fumaric acid) |
| 22 | —CH$_2$—CH$_2$—N(CH$_3$)$_2$ | | | 105–107 | 328 (M$^+$) |
| 23 | —CH$_2$CH$_2$N(piperidine) | | | 110.5–112 | 368 (M$^+$) |
| 24 | —CH$_2$COOCH$_3$ | | | 110.5–112.5 | 329 (M$^+$) |
| 25 | —CON(CH$_3$)$_2$ | | | 141 (dec.) | 328 (M$^+$) |
| 26 | —CSN(CH$_3$)$_2$ | | | 107–109 | 344 (M$^+$) |
| 27 | —CH$_2$—C$_6$H$_4$(NHCOC$_2$H$_5$) | | | 161 (dec.) | 418 (M$^+$) |

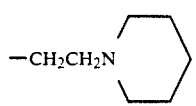

| | R | R$_1$ | R$_3$ | | |
|---|---|---|---|---|---|
| 28 | —CH$_3$ | —C$_6$H$_5$ | H | 219–220 | 326 (M$^+$) |
| 29 | —CH$_2$—CH$_2$—CH$_3$ | —C$_6$H$_5$ | H | 158–159 | 319 (M$^+$) |
| 30 | —CH$_2$—CH=CH$_2$ | —C$_6$H$_5$ | H | 126–128 | 317 (M$^+$) |
| 31 | —CH$_2$~CH=CH—CH$_3$ | —C$_6$H$_5$ | H | 150–15 | 331 (M$^+$) |
| 32 | —CH$_2$—C≡CH | —C$_6$H$_5$ | H | 139 (dec.) | 315 (M$^+$) |
| 33 | —CH$_2$—C≡C—CH$_3$ | —C$_6$H$_5$ | H | 184–185 | 329 (M$^+$) |
| 34 | —COCH$_3$ | —C$_6$H$_5$ | H | 189–191 | 319 (M$^+$) |
| 35 | —COC$_2$H$_5$ | —C$_6$H$_5$ | H | 179–181 | 333 (M$^+$) |
| 36 | —COC(CH$_3$)$_3$ | —C$_6$H$_5$ | H | 209–211 | 361 (M$^+$) |
| 37 | —COCH=CH$_2$ | —C$_6$H$_5$ | H | 199–201 | 331 (M$^+$) |
| 38 | —CO—C(H)=C(CH$_3$)(H) | —C$_6$H$_5$ | H | 181–182 | 345 (M$^+$) |
| 39 | —CH$_2$—CH$_2$—N(CH$_3$)$_2$ | —C$_6$H$_5$ | H | 142–143.5 | 348 (M$^+$) |
| 40 | —CH$_2$—CH$_2$—N(piperidine) | —C$_6$H$_5$ | H | 163–164 | 388 (M$^+$) |
| 41 | —CH$_2$CN | —C$_6$H$_5$ | H | 189–190 | 316 (M$^+$) |
| 42 | —CH$_2$—COOCH$_3$ | —C$_6$H$_5$ | H | 155–156 | 349 (M$^+$) |
| 43 | —COCH$_2$—OCH$_3$ | —C$_6$H$_5$ | H | 178–179 | 349 (M$^+$) |
| 44 | —COCH$_2$—CH$_2$—OCH$_3$ | —C$_6$H$_5$ | H | 165–166 | 363 (M$^+$) |
| 45 | —CON(CH$_3$)$_2$ | —C$_6$H$_5$ | H | 174–175.5 | 348 (M$^+$) |
| 46 | —CSN(CH$_3$)$_2$ | —C$_6$H$_5$ | H | 202–203 | 364 (M$^+$) |
| 47 | —COOC$_2$H$_5$ | —C$_6$H$_5$ | H | 183–184.5 | 349 (M$^+$) |
| 48 | —CO—(2-pyridyl) | —C$_6$H$_5$ | H | 213–214 | 382 (M$^+$) |
| 49 | —CO—C$_6$H$_5$ | —C$_6$H$_5$ | H | 193 | 381 (M$^+$) |

TABLE 3-continued

| Compds. No. | | | | m.p. (°C.) | M.S. (m/e) |
|---|---|---|---|---|---|
| 50 | —CH₂—C₆H₄(NHCOC₂H₅) (o-) | —C₆H₅ | H | 151–152 | 438 (M⁺) |
| 51 | —COC₃H₇ | —C₆H₅ | H | 190–191 | 347 (M⁺) |
| 52 | —CO—C₂H₅ | —C₆H₅ | 7-CH(CH₃)₂ | 144–145 | 375 (M⁺) |
| 53 | —CO—C₄H₉ | —C₆H₅ | 7-CH(CH₃)₂ | 93–94 | 403 (M⁺) |
| 54 | —CO—C₂H₅ | —C₆H₄—OCH₃ (p-) | H | 205–207 | 309 (M⁺) |
| 55 | —CO—CH₃ | —C₆H₄—F (p-) | H | 199–200 | 337 (M⁺) |
| 56 | —CO—C₂H₅ | —C₆H₄—F (p-) | H | 211 | 351 (M⁺) |
| 57 | —CO—CH₃ | —C₆H₄—Cl (p-) | H | 202–203 | 353 (M⁺) |
| 58 | —CO—C₂H₅ | —C₆H₄—Cl (p-) | H | 211 | 367 (M⁺) |
| 59 | —CO—C₂H₅ | —C₆H₄—F (p-) | 7-CH(CH₃)₂ | 186–188 | 393 (M⁺) |
| 60 | H\C=C/COOH, CH₃/  \H | —CH₃ | H | 285 (dec.) | 285 (M⁺) |
| 61 | —CH₂—CH=CH₂ | —CH₃ | H | 136–138 | 255 (M⁺) |
| 62 | —CH₂—CH=CH—CH₃ | —CH₃ | H | 145–146 | 269 (M⁺) |
| 63 | —CH₂—C≡CH | —CH₃ | H | 131 (dec.) | 253 (M⁺) |
| 64 | —CH₂—C≡C—CH₃ | —CH₃ | H | 149–150 | 267 (M⁺) |
| 65 | —COCH₃ | —CH₃ | H | 172 (dec.) | 257 (M⁺) |
| 66 | —COC₂H₅ | —CH₃ | H | 171 (dec.) | 271 (M⁺) |
| 67 | —COC₃H₇ | —CH₃ | H | 158–159 | 285 (M⁺) |
| 68 | —COC(CH₃)₃ | —CH₃ | H | 191–192 | 299 (M⁺) |
| 69 | H\C=C/CH₃, —CO/  \H | —CH₃ | H | 132–133 | 283 (M⁺) |
| 70 | —CH₂—CH₂—N(CH₃)₂ | —CH₃ | H | 142–143.5 | 286 (M⁺) |

TABLE 3-continued

| Compds. No. | R | R$_1$ | R$_2$ | m.p. (°C.) | M.S. (m/e) |
|---|---|---|---|---|---|
| 71 | −CH$_2$−CH$_2$−N(piperidine) | −CH$_3$ | H | 138−139 | 326 (M$^+$) |
| 72 | −COCH$_2$−OCH$_3$ | −CH$_3$ | H | 160−161 | 287 (M$^+$) |
| 73 | −CON(CH$_3$)$_2$ | −CH$_3$ | H | 165 (dec.) | 286 (M$^+$) |
| 74 | −CSN(CH$_3$)$_2$ | −CH$_3$ | H | 183 (dec.) | 302 (M$^+$) |
| 75 | −COCH$_2$−CH$_2$−OCH$_3$ | −CH$_3$ | H | 152−153 | 301 (M$^+$) |
| 76 | −CO−(2-pyridyl) | −CH$_3$ | H | 201 (dec.) | 320 (M$^+$) |
| 77 | −CO−C$_6$H$_5$ | −CH$_3$ | H | 190−192 | 319 (M$^+$) |
| 78 | −CH$_2$−(2-NHCOC$_2$H$_5$-C$_6$H$_4$) | −CH$_3$ | H | 204−205 | 376 (M$^+$) |
| 79 | −CH$_2$CN | −CH$_3$ | H | 206−207 | 254 (M$^+$) |
| 80 | −CH$_2$−COOCH$_3$ | −CH$_3$ | H | 137−138 | 287 (M$^+$) |
| 81 | −CO−CH(CH$_3$)$_2$ | −CH$_3$ | H | 182−183 | 285 (M$^+$) |
| 82 | −CO−C$_4$H$_9$ | −CH$_3$ | H | 158 | 299 (M$^+$) |
| 83 | −CO−(4-OCH$_3$-C$_6$H$_4$) | −CH$_3$ | H | 182−183 | 285 (M$^+$) |
| 84 | −CO−(4-F-C$_6$H$_4$) | −CH$_3$ | H | 192−193 | 337 (M$^+$) |
| 85 | −CO−(4-Cl-C$_6$H$_4$) | −CH$_3$ | H | 189−191 | 353 (M$^+$) |
| 86 | −CO−C$_6$H$_5$ | −CH$_3$ | 7-CH(CH$_3$)$_2$ | 141−142 | 361 (M$^+$) |

| | R | R$_1$ | R$_2$ | | |
|---|---|---|---|---|---|
| 87 | −COC$_2$H$_5$ | −C$_6$H$_5$ | −CH$_3$ | 223−224 | 335 (M$^+$) |

TABLE 3-continued

| Compds. No. | | | | m.p. (°C.) | M.S. (m/e) |
|---|---|---|---|---|---|
| 88 | —COC₂H₅ | —CH₃ | —CH₃ | 102–104 | 273 (M⁺) |
| 89 | —COCH₂—OCH₃ | —C₆H₅ | —CH₃ | 119–121 | 351 (M⁺) |

| | R | R₁ | R₂ | | |
|---|---|---|---|---|---|
| 90 | —COC₂H₅ | —C₆H₅ | —CH₃ | 118–119 | 285 (M⁺) |
| 91 | —COC₂H₅ | —CH₃ | —CH₃ | Oil | 223 (M⁺) |
| 92 | —COCH₂—O—C₆H₅ | —C₆H₅ | —CH₃ | 112–113 | 363 (M⁺) |

What is claimed is:

1. A compound of the formula:

A—S—R wherein:

A is

R represents a lower alkyl, alkenyl, alkynyl, alkanoyl, alkenoyl, dialkylaminoalkyl, cyanoalkyl, alkoxycarbonylalkyl, carboxy alkenyl, alkoxycarbonyl, alkoxyalkylcarbonyl, dialkylaminocarbonyl, dialkylaminothiocarbonyl, phenoxyalkylcarbonyl, piperidinoalkyl, pyridine carbonyl, substituted or unsubstituted benzoyl, or substituted or unsubstituted benzyl group, and pharmaceutically acceptable acid addition salts thereof.

2. A compound according to claim 1 wherein:
A is

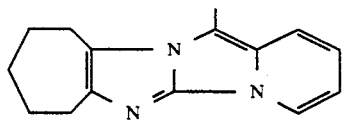

and represents an alkenyl, alkynyl, alkanoyl, cyanoalkyl, dialkylaminoalkyl, piperidinoalkyl, alkoxycarbonylalkyl, dialkylaminocarbonyl, dialkylthiocarbonyl or N-alkanoylaminobenzyl group, and pharmaceutically acceptable acid addition salts thereof.

3. A compound according to claim 1 wherein:
A is

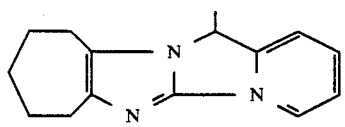

and represents a propenyl, propynyl, cyanomethyl, butenyl, butynyl, acetyl, propionyl, dimethylaminoethyl, piperidino, methoxycarbonylmethyl, dimethylaminocarbonyl, dimethylaminothiocarbonyl or N-propionylaminobenzyl group.

4. An anti-gastric ulcerative agent comprising a pharmaceutically acceptable carrier and as an active ingredient a compound defined in claim 1 in an amount effective to inhibit gastric ulcer.

5. Pyrido[1′,2′:3,4]imidazo[1,2-a]-7,8,9,10,11-pentahydrocycloheptimidazol.

* * * * *